United States Patent
St. Martin et al.

(10) Patent No.: US 8,580,096 B2
(45) Date of Patent: Nov. 12, 2013

(54) BIOPROCESS UTILIZING CARBON DIOXIDE AND ELECTRODEIONIZATION

(75) Inventors: Edward J. St. Martin, Libertyville, IL (US); YuPo J. Lin, Naperville, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 126 days.

(21) Appl. No.: 13/248,231

(22) Filed: Sep. 29, 2011

(65) Prior Publication Data

US 2013/0081947 A1    Apr. 4, 2013

(51) Int. Cl.
*B01D 61/48* (2006.01)

(52) U.S. Cl.
USPC ........... 204/524; 204/530; 204/533; 204/536; 204/632

(58) Field of Classification Search
USPC .................. 204/524, 530, 533, 536, 632
See application file for complete search history.

(56) References Cited

U.S. PATENT DOCUMENTS

| | | |
|---|---|---|
| 5,034,105 A | 7/1991 | Berglund et al. |
| 5,143,834 A | 9/1992 | Glassner et al. |
| 5,869,301 A | 2/1999 | Nghiem et al. |
| 6,495,014 B1 | 12/2002 | Datta et al. |
| 6,743,610 B2 | 6/2004 | Donnelly et al. |
| 6,797,140 B2 | 9/2004 | Lin et al. |
| 7,141,154 B2 | 11/2006 | Lin et al. |
| 7,915,447 B2 | 3/2011 | Fujita et al. |
| 8,007,647 B2 * | 8/2011 | Lin et al. ............... 204/536 |
| 2004/0060875 A1 | 4/2004 | Lin et al. |
| 2008/0187902 A1 | 8/2008 | Liu et al. |
| 2010/0297715 A1 | 11/2010 | Dehay et al. |

* cited by examiner

*Primary Examiner* — Arun S Phasge
(74) *Attorney, Agent, or Firm* — Olson & Cepuritis, Ltd.

(57) ABSTRACT

A method for producing succinic acid is provided, which comprises circulating a fermentation broth containing succinate ion through an electrodeionization apparatus. The apparatus comprises an anode; a cathode; a stacked ion-exchange assembly comprising a one or more oriented ion-exchange units between the anode and the cathode. Each ion-exchange unit comprises a porous ion-exchange resin wafer including an inlet and an outlet together are adapted to circulate a liquid reaction stream containing a carboxylate anion from a fermentor through the resin wafer; a flow-distributing gasket for circulating a product stream through a product reservoir; an anion exchange membrane for transporting at least a portion of the carboxylate anion to the product stream; and a bipolar ion-exchange membrane to direct protons toward the cathode and into the product stream and to direct hydroxyl ions toward the anode and into the reaction stream in the resin wafer of an adjacent ion-exchange unit.

14 Claims, 5 Drawing Sheets

BIOPROCESS UTILIZING CARBON DIOXIDE AND ELECTRODEIONIZATION

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to methods of preparing succinic acid. More particularly, this inventions relates to the preparation of succinic acid utilizing electrodeionization (EDI).

BACKGROUND OF THE INVENTION

Electrodeionization (EDI), also known as electrochemical ion-exchange, is an advanced ion-exchange technology that combines the advantages of ion-exchange and electrodialysis. In an electrodeionization process, ion exchange resins are sequestered in dilute compartments to increase ionic conductivity, so that even with very dilute ionic feed (e.g., about $10^{-5}$N), a stable operation with higher ion separation flux and lower energy consumption than electrodialysis becomes possible. EDI technology is presently used to make deionized water for boiler feed and high purity and industrial water applications. However, there are also other uses and potential uses of such technology for processing organic product streams in a variety of industries. Some of these technologies have been touched on by patents and patent applications filed on behalf of Argonne National Laboratory (ANL) such as, for example U.S. Pat. No. 6,797,140, U.S. Pat. No. 6,495,014, and U.S. Pat. No. 8,007,647, the entire disclosures of each of these references being herein incorporated by reference.

In many fermentation and enzymatic processes a high (e.g., millimolar) concentration of medium components must be maintained. Common examples are monovalent and divalent cations and anions that provide an appropriate required ionic environment for optimum activity of microorganisms and enzymes. These monovalent and divalent cations and anions are identified as counter-ions hereinafter. The concentrations of the counter-ions in the fermentation reaction medium should be maintained within a predetermined range to ensure optimum reaction conditions. Diminishing counter-ion concentration in the fermentation broth or reaction medium can be a serious problem, because replacement of the counter-ions in a flow-through system would be expensive and would prohibitively increase the cost of obtaining the fermentation product. There is an ongoing need for new, more efficient processes for producing organic acids such as succinic acid. The present invention addresses this need.

SUMMARY OF THE INVENTION

This invention relates to an improved process for the production of organic acids. More specifically this invention provides an improved bioprocess for the production of succinic acid ($C_4H_6O_4$). Some microorganisms are capable of fixing carbon dioxide ($CO_2$) that is present in the atmosphere, to synthesize bio-based chemicals. For example: the synthesis of 2 moles of succinic acid from 1 mole of glucose and 2 moles of $CO_2$. Succinic acid is currently made using standard fermentation and separation technology to yield the calcium or sodium succinate. Succinate salts are used as deicers and for other specialty product purposes. A more facile method of producing of succinic acid in its acid form is desirable to lower manufacturing complexity and costs. Improved processes for producing succinic acid could also open up larger market opportunities, e.g., as a renewable (non-petroleum) source of maleic anhydride or butanediol. Current fermentation processes for the production of succinic acid use microorganisms that are grown anaerobically in batch cultures in a complex medium that contains a mixture of nutrients. The fermentation medium must be supplied with a feedstock containing $CO_2$ and glucose, and must be neutralized with a base (e.g., sodium hydroxide, calcium hydroxide, sodium carbonate and/or calcium carbonate) as the succinic acid is formed.

Sodium and/or calcium succinate salts accumulating in the fermentor can inhibit the fermentation process and limit succinate production. The succinate product (as the Na or Ca salt) from such conventional fermentation processes must then be separated from the cellular components of the fermentation broth and from the complex growth medium components. The succinate salts typically are concentrated by removing most of the water, and then are fractionally precipitated to obtain a more purified salt. In order to produce free succinic acid, the metal counter-ion of the succinate salt must then be exchanged with a concentrated acid such as sulfuric acid. This process results in the production of a metal sulfate as a waste product.

Another method of purifying succinic acid utilizes electrodialysis to concentrate the succinate salt, followed by water-splitting electrodialysis to obtain the free succinic acid. The use of electrodialysis to capture the succinate that is produced by fermentation requires that high concentrations of the succinate ions be achieved in a batch reactor in order to be economically viable. Electrodialysis is not capable of removing low concentrations of succinate that are produced in a continuous bioreactor process. All of the above methods involve several unit operations and require the addition of acids and/or bases to achieve the production and purification of succinic acid. The methods of the present invention provide more direct and continuous processes to directly obtain the acid form of succinic acid. The methods of the present invention eliminate many of the above-described unit operations of the conventional fermentation, separation, and chemical conversion processes, and yield purified succinic acid as the final product.

In one embodiment, the present invention provides a method for preparing succinic acid in a bioreactor comprising an EDI apparatus in which succinic acid is isolated in the acid form directly from the bioreactor. The EDI apparatus comprises: (a) an anode; (b) a cathode; (c) a stacked ion-exchange assembly between the anode and the cathode, the stacked ion-exchange assembly comprising one or more oriented ion exchange units; and (d) a bipolar membrane separating the cathode from the stacked ion-exchange assembly. Each ion-exchange unit comprises: (i) a porous ion-exchange resin wafer including an inlet and an outlet, wherein the inlet and outlet together are adapted to circulate a liquid recycle stream containing a product anion (e.g., succinate) from a fermentor through the resin wafer and back into the fermentor; (ii) a flow-distributing gasket adapted to circulate a product stream through a product reservoir; (iii) an anion exchange membrane adapted to transport at least a portion of the product anion to the product stream when present in the flow-distributing gasket; and (iv) a bipolar ion-exchange membrane adapted to generate protons toward the cathode and into the product stream to combine with the product anion (e.g., to form a succinic acid) and to generate hydroxyl ions toward the anode and into the recycle stream in the resin wafer of an adjacent ion-exchange unit. In each ion exchange unit, the anion exchange membrane is situated between the flow-distributing gasket and the wafer, and the flow-distributing gasket is disposed between the bipolar ion-exchange membrane and the anion exchange membrane. Preferably the stacked ion exchange assembly comprises 2 or more ion-exchange units. Each ion exchange unit is oriented with the wafer facing the cathode and the bipolar ion-exchange membrane facing the anode.

The protons and hydroxyl ions are formed by an electrochemical water splitting reaction on the bipolar ion-exchange membrane (IEM) when an electric potential is applied across the anode and the cathode. In some preferred embodiments the EDI apparatus further comprises (e) a first flow-distributor between the anode and the stacked ion-exchange assembly closest to the anode; and (f) a second flow-distributor between the cathode and the bipolar membrane separating the cathode from the stacked ion-exchange assembly, e.g., to facilitate rinsing of the electrodes.

In one method aspect of the present invention, succinic acid, in its acid form, is produced by circulating at least the liquid phase of an anaerobic fermentation broth from a fermentor (e.g., a fermentation vessel) through the stacked ion-exchange assembly of the EDI apparatus described herein, while applying an electric potential between the anode and cathode of the EDI apparatus. The fermentation broth comprises bacteria genetically modified to produce succinic acid from a feedstock comprising glucose and a source of carbonate. The succinic acid in the broth is produced initially in the anionic form. In some embodiments, the cellular component of the fermentation broth is retained in a fermentor and only the soluble portion of the broth is circulated through the stacked ion-exchange assembly. In other embodiments, the entire broth, including the bacterial cells, is circulated through the stacked ion-exchange assembly. The source of carbonate in the feedstock can be carbon dioxide (e.g., dissolved in water), or a carbonate salt (e.g., sodium, potassium, calcium, and/or magnesium carbonate or bicarbonate).

A preferred method of directly producing the acid form of succinic acid comprises circulating the liquid phase of an aqueous, anaerobic fermentation broth from a fermentor into the stacked ion-exchange assembly of the EDI apparatus as described herein while applying an electric potential across the anode and cathode of the EDI apparatus and supplying glucose and a carbonate source to the fermentation broth. Thee fermentation broth comprises glucose, carbonate ions, and an aqueous suspension of $E.\ coli$ bacteria genetically modified to produce succinic acid from glucose and carbonate, the pH of the fermentation broth being maintained at a pH in the range of about 6 to about 7 by addition of an aqueous base into the fermentor from a base reservoir. The succinate ions produced by the bacteria are separated from the fermentation broth by the anion exchange membranes of the ion-exchange units and are combined with protons from an electrochemical water splitting reaction to form succinic acid in a product stream that is circulated into a product collection vessel. Alkali metal and/or alkaline earth metal ions (preferably sodium ions) in the fermentation broth are combined with hydroxyl ions from the water splitting reaction to form a solution of a metal hydroxide, which is recycled into the base reservoir. The protons and hydroxyl ions are generated by the water splitting reaction on the bipolar IEM and separated from each other by the bipolar membranes of the ion-exchange units with the protons migrating toward the direction of the cathode (negative electrode) and the hydroxyl ions migrating toward the direction of the anode (positive electrode).

The modified-bacteria preferably comprise $Escherichia\ coli$ having mutations in the genes ptsG, pflB, and ldhA, such as $E.\ coli$ strains AFP 184, AFP 400, or AFP 404 described in U.S. Pat. No. 6,743,610 to Donnelly et al., which is incorporated herein by reference in its entirety.

During operation, protons and hydroxyl ions are formed by the water splitting reaction discussed above. The protons migrate across the bipolar membranes of the EDI apparatus in the direction of the cathode, while the generated hydroxyl ions migrate from the surface of the bipolar membranes in the direction of the anode. Succinate ions are separated from the fermentation broth by the anion exchange membranes of the EDI apparatus and are combined with protons from the water splitting reaction to form succinic acid (in the acid form) in the product stream. The product stream is circulated to a collection vessel. Cations such as sodium combine with the hydroxyl ions from the water slitting reaction to form the basic recycle stream, which is eventually recirculated back into the fermentor to maintain the pH of the fermentation broth at about pH 6.5.

Preferably, the ion-exchange resin is present in the wafers at a concentration in the range of about 30 to 80 percent by weight (wt %), e.g., about 55 to 70 wt %. The wafers preferably are flexible porous ion-exchange material containing one or more of anion-exchange moieties or cation-exchange moieties or mixtures thereof immobilized with respect to each other with a binder comprising from about 25 wt % to about 45 wt % by weight of the porous ion-exchange material without substantially coating the moieties.

In some preferred embodiments, the porous wafers have at least 15% porosity and the binder is present in a weight ratio to the moieties of about 1:3.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE PRESENT INVENTION

The present invention provides an integrated process that utilizes an electrodeionization (EDI) apparatus to provide for continuous production, removal and concentration of succinic acid product from a fermentation reaction. Because the succinic is captured in the acid form and not the usual salt form obtained from conventional fermentation processes, a separate chemical conversion of the succinate salt is not needed and no waste salt byproducts are formed. The EDI apparatus is configured to allow continuous capture and retention of the metal counter-ions (e.g., Na or Ca ions) back into a fermentor where the succinate is formed. For example, sodium ion is retained and recycled as NaOH to provide pH control for the fermentation reaction medium in the fermentor. In addition, the recycle of the Na counter-ion is also used to capture and concentrate $CO_2$ as sodium carbonate to provide a concentrated supply of $CO_2$ for the fermentation feedstock.

Modified *E. coli* strains described by Donnelly et al.(U.S. Pat. No. 6,743,610) can produce succinic acid from $CO_2$ and glucose without the need of a complex growth medium. The synthesis of succinic acid is uncoupled from the need to have the cells growing, as is the case in a conventional batch fermentation process. This allows a bioreactor that contains the cells to be run in a continuous manner for the production of succinic acid and does not require the continuous re-growth of individual batches of cells. The pH of the fermentation broth is maintained at about 6.5 by controlled addition of the $CO_2$ and basic feed stocks and removal of succinate product during the reaction.

Certain aspects of the present invention are illustrated by reference to the drawing figures, in which components of the same or similar function are identified by reference numbers having the same final two digits.

Figure 1:
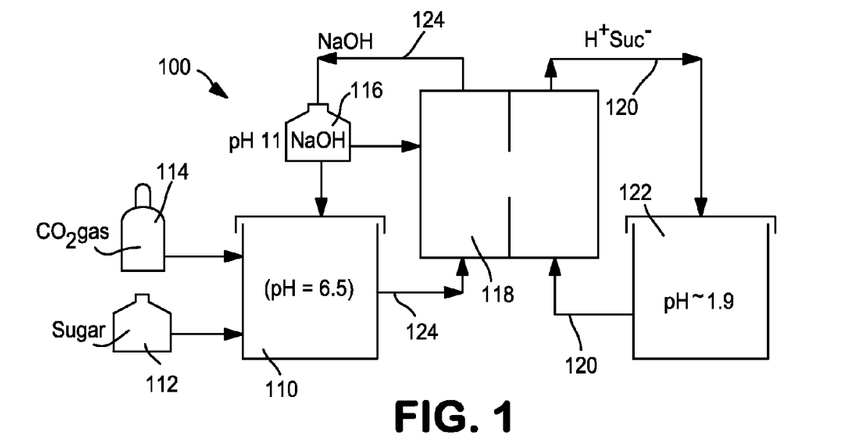
FIG. 1 is a schematic illustration of separative bioreactor system using an EDI apparatus for the production of succinic acid.

FIG. 1 provides a schematic illustration of a separative bioreactor system 100 comprising an EDI apparatus, which is useful for producing succinic acid. Separative bioreactor system 100 comprises a fermentor 110 containing an aqueous fermentation broth for producing succinate. Glucose is fed into fermentor 110 from supply vessel 112, while $CO_2$ is fed into fermentor 110 from supply tank 114 as a source of carbonate (e.g., carbon dioxide, bicarbonate, and or carbonate ion). Sodium hydroxide is fed into fermentor 110 from reservoir 116 to control the pH in the broth at a pH of about 6 to 7 (e.g., about 6.5). The fermentation broth comprises modified *E. coli* cells adapted to produce succinate from the glucose and carbonate feedstock. The liquid phase of the fermentation broth is circulated into an EDI apparatus 118, where an anion exchange membrane separates succinate anion from counter-cations such as sodium ion. Preferably, particulates are removed from the liquid prior to feeding into the EDI apparatus. The succinate is combined with protons generated by an electrochemical water splitting reaction during operation of the EDI apparatus to form succinic acid, which is transported by product stream 120 into receiving tank 122. Hydroxide ions formed from the water splitting reaction are combined with the counter-cations to form a basic solution (e.g., NaOH), which is circulated in recycle stream 124 back into reservoir 116. The circulation of the fermentation broth, reaction stream, product stream, and feed stocks (e.g., glucose and sodium hydroxide) can be facilitated by pumps, if desired.

Figure 2:
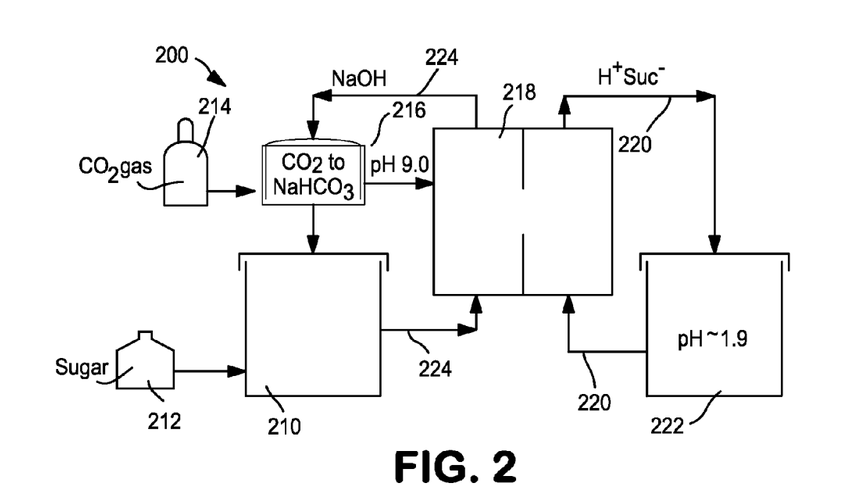
FIG. 2 is a schematic illustration of an alternative configuration of a separative bioreactor system using an EDI apparatus for the production of succinic acid.

FIG. 2 provides a schematic illustration of an alternative separative bioreactor system 200 comprising an EDI apparatus, which is useful for producing succinic acid. Separative bioreactor system 200 comprises a fermentor 210 containing an aqueous fermentation broth for producing succinate. Glucose is fed into fermentor 210 from supply vessel 212, while $CO_2$ is fed from supply tank 214 into reservoir 216, which also contains a base such as sodium hydroxide, to form a carbonate solution, which is fed into fermentor 210 to control the pH in the broth at a pH of about 6.5 and to supply the necessary carbonate for the production of succinate. The liquid phase of the fermentation broth is circulated into EDI apparatus 218, which separates succinate anion from counter-cations such as sodium ion. Preferably, particulates are removed from the liquid prior to feeding into the EDI apparatus. The succinate is combined with protons generated by an electrochemical water splitting reaction during operation of the EDI apparatus to form succinic acid, which is transported by product stream 220 into receiving tank 222. Hydroxide ions formed from the water splitting reaction are combined with the counter-cations to form a basic solution (e.g., NaOH), which is circulated in recycle stream 224 back into reservoir 216. The circulation of the fermentation broth, reaction stream, product stream, and feed stocks (e.g., glucose and sodium hydroxide) can be facilitated by pumps, if desired.

In FIG. 2, the process works substantially as described above with respect to FIG. 1, except that carbon dioxide is fed into base reservoir 216 to produce carbonate ions, which is then fed into bioreactor 210 as the $CO_2$ source for the fermentation. The NaOH in the recycle stream is neutralized with a controlled amount of $CO_2$ to yield a carbonate solution at a pH of about 9. The carbonate solution in base reservoir 216 is reused in the bioreactor with additional glucose substrate to provide a continuous succinic acid production process. This process provides a continuous and controlled supply of carbonate for the bioreactor and avoids using extensive mixing and pressure to provide sufficient $CO_2$ for the bioreactor. In addition, the carbonate retention and recycle provide for some internal buffering for the succinic acid that is produced by the fermentation reaction.

Figure 3:
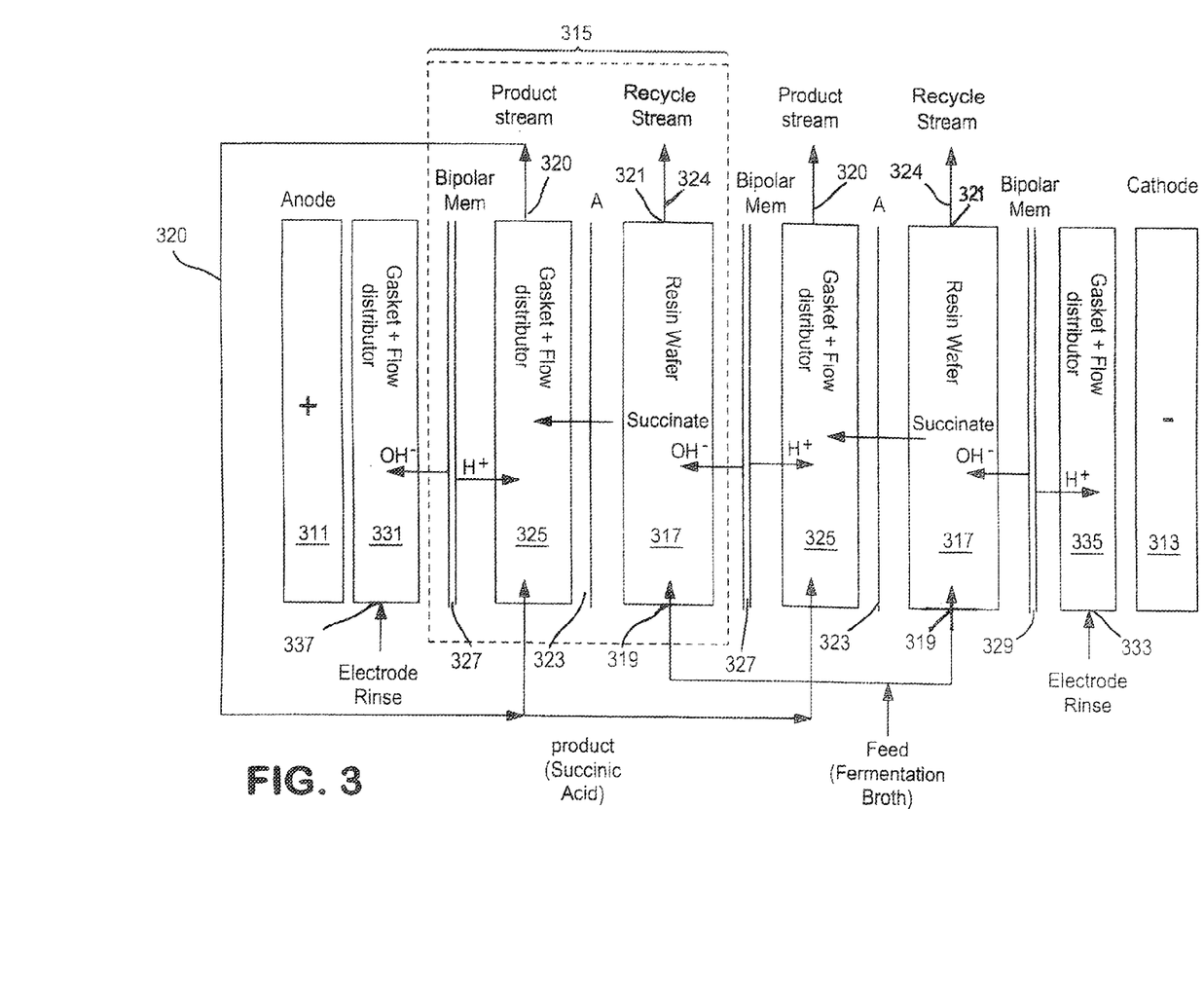
FIG. 3 is a schematic diagram of an EDI apparatus for use in the production of succinic acid.

The details of an EDI apparatus useful in the systems and methods of the present invention are schematically illustrated in FIG. 3. EDI apparatus 318 comprises anode 311, cathode 313, and a stacked assembly of ion-exchange units 315 between anode 311 and cathode 313. Each ion-exchange unit 315 comprises porous resin wafer 317, anion-exchange membrane 323, flow-distributing gasket 325 and bipolar membrane 327. Wafer 317 includes an inlet 319 and an outlet 321. Anion-exchange membrane 323 and flow flow-distributing gasket 325 are situated between wafer 317 and bipolar membrane 325, with gasket 325 adjacent bipolar membrane 325 and anion-exchange membrane 323 between wafer 317 and gasket 325. Each ion-exchange unit is oriented with wafer 317 facing cathode 313 and bipolar membrane 327 facing anode 311. Flow distributor 331 is situated between anode 311 and the bipolar membrane 327 of the ion-exchange unit 315 closest to anode 311 to facilitate rinsing of anode 311. Flow distributor 335 and bipolar membrane 329 are situated between cathode 313 and the wafer 317 of the ion-exchange unit 315 closest to cathode 313 to facilitate rinsing of cathode 313. Flow distributor 335 is disposed between membrane 329 and cathode 313.

In use, an electric potential of about 3 to about 12 Volts per resin wafer set is applied across anode 311 and cathode 313 while a fermentation broth comprising succinate anions is fed into porous resin wafers 317 via inlets 319. An electrochemical water splitting reaction generates protons and hydroxide ions. The protons flow in the direction of the cathode and the hydroxyl ions flow in the direction of the anode, through bipolar membranes 327. Succinate ion is transported across anion-exchange membranes 323 into flow-distributing gaskets 325, where the succinate is combined with the protons to form succinic acid, which is then distributed into product stream 320 in a chambers created by gaskets 325. At the same time, the succinate ion from the fermentation broth in wafers 317 is replaced by the hydroxide ions, and the resulting succinate-depleted broth is injected into recycle stream 324 through outlets 321.

Preferably, resin wafers 317 have a porosity in the range of between 15% to about 60% and contain one or more of anionic exchange moieties or cationic exchange moieties or mixtures thereof immobilized with respect to each other with a binder comprising about 25% to about 45% by weight of the porous ion exchange material without substantially coating the moieties. More preferably, each of the porous resin wafers 317 has a porosity of at least 15% and the binder is preferably present in a weight ratio to the moieties of about 1:3. The ion exchange resin wafers contain one or more of a strong acid resin, a weak acid resin, a strong basic resin or a weak basic resin and the ion exchange resins are preferably present in the range of from about 30% to about 80% by weight of the wafers 317 and most preferably in the range of about 55% to about 70% by weight of the wafers. Preferably, the resin wafers 317 comprise cationic and anionic exchange moieties in a ratio of about 1.3:1, cationic-to-anionic exchange moieties.

A noted above, some microorganisms are capable of fixing carbon dioxide ($CO_2$) that is present in the atmosphere to synthesize succinic acid (2 moles of succinic acid are produced from 1 mole of glucose and 2 moles of $CO_2$). The synthesis rate is limited by the low level of $CO_2$ in the atmosphere and the poor solubility of $CO_2$ in water at metabolically relevant pH values. The reaction can be enhanced by concentrating the $CO_2$ and by aggressive mixing to saturate the fermentation broth. However, the limited solubility in water is still a problem in acidic environments. Basic solutions that contain for example $Na^+$, $NH_4^+$, $Mg^{2+}$, or $Ca^{2+}$ hydroxide can be used to increase the $CO_2$ concentration as carbonate or bicarbonate ($HCO_3^-$) in solution. As used herein, the term "carbonate" refers collectively to $CO_2^{2-}$ and $HCO_2^-$ for convenience, unless otherwise specified. Thus, the following reactions (1), (2) and (3):

$$CO_2 + H_2O = [HCO_3]^-[H]^+ \quad (1)$$

$$[HCO_3]^-[H]^+ + NaOH = [HCO_3]^-[Na]^+ + H_2O \quad (2)$$

$$[HCO_3]^-[Na]^+ + NaOH = [CO_3]^{2-}[Na]_2^+ + H_2O \quad (3)$$

are in equilibrium in solution. As the microorganisms utilize carbonate and produce succinic acid, the pH of the solution drops and more of carbonate ion will be shifted to a mixture of bicarbonate and carbonate ions. This allows one to use addition of carbonate into the bioreactor to both partially control the pH of the fermentation medium and to provide a high concentration of carbonate for the synthesis of succinic acid. However, the addition of sodium carbonate cannot be used in a conventional batch fermentation process, because the accumulation of sodium succinate in the fermentation medium inhibits the fermentation reaction.

The following examples are provided to illustrate certain aspects and features of the present invention, and are not to be construed as limiting the invention as set forth in the appended claims.

EXAMPLE 1

Conventional Batch Fermentation

The synthesis of succinic acid by bacterial strain AFP 184 was examined in a medium that did not contain any nutrients and therefore did not allow the cells to grow. The succinic acid synthesis was thus uncoupled from the cell growth.

A small amount (about $10^8$ cells) of AFP184 was cultured from a frozen glycerol sample in about 2.5 mL of sterile Luria Broth (LB; comprising tryptone, yeast extract, and sodium chloride) in a 15 mL sterile test tube and incubated overnight with shaking at about 200 revolutions-per-minute (rpm), at about 30° C. The next day the entire 2.5 mL inoculum was subcultured into about 1000 mL LB in a 2 L-baffled shaker flask at about 37° C. with shaking at about 250 rpm for about 4 to 6 hours. The cells were harvested after achieving an optical density at 600 nm (OD600) of about 3 to 5, by transferring cells to centrifuge bottles that hold about 200 to 300 mL of liquid and centrifuging at about 4000 rpm for about 30 minutes. The supernatant was discarded and the resulting cell pellet was resuspended in about 5 to 10 mL of 5 millimolar (mM) phosphate buffer. The buffered suspension was used to inoculate about 300 mL of 5 mM phosphate buffer in a fermentor. The yield was about 8 to 10 grams of cells per liter (g/L).

The fermentation medium was prepared with about 250 to 300 mL of 5 mM phosphate and the pH was adjusted to about 6 to 7 with 0.1 M sodium carbonate. The small amount of phosphate in the fermentation medium was used to control the initial pH of the mixture. This mixture was then added to a 500 mL fermentor (also referred to herein as a "fermentation bioreactor" or "bioreactor" for convenience) with a calibrated pH probe and autoclaved. The fermentation was operated under an anaerobic atmosphere by bubbling a 90% nitrogen and 10% $CO_2$ gas mixture into the fermentor. The succinic acid synthesis was initiated by feeding a concentrated glucose solution (about 200 g/L to 500 g/L) into the fermentor, which was maintained at about 30° C., and was stirred at about 100 rpm. About 0.05 M carbonate was used to control the pH of the medium in the fermentor in the range of about 6 to 7.

Figure 4:
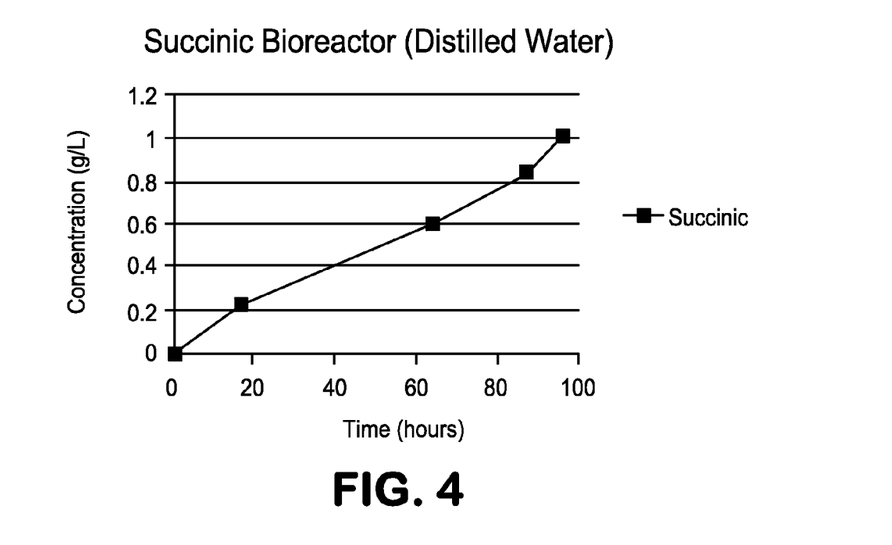
FIG. 4 provides a graph of succinic acid concentration produced by microbial cells in distilled water without the need of a nutrient rich growth medium in a batch fermentation without an EDI apparatus.

The succiniate concentration in the fermentation medium was monitored for about 100 hours by high performance liquid chromatography (HPLC). A graph of the succinate concentration versus time is shown in FIG. 4. The results in FIG. 4 demonstrate that the modified *E. coli* cells were able to synthesize succinate continuously over the 100 hour period and reached a final concentration of about 1 gram-per-liter (g/L). Only trace amounts of other fermentation products were detected. These results confirm the ability of AFP 184 cells to produce succinate in a non-growth medium with very little added nutrients other than glucose and carbon dioxide.

EXAMPLE 2

Continuous Fermentation in EDI Bioreactor

The synthesis of succinic acid by bacterial strain AFP184 was examined in a non-growth medium, as in Example 1, but utilizing an EDI bioreactor system for continuous succinic acid production. A non-growth fermentation medium is preferred as the feedstock for the EDI apparatus in the methods of the present invention to capture and concentrate succinic acid as it is produced in the bioreactor.

The EDI bioreactor system provided for capture and retention of the $Na^+$ and its recycle as NaOH, to be used to control the pH of the fermentation medium during succinate production. An inoculum of AFP 184 cells was established in a non-growth medium in a fermentor, and a mixture of 10% $CO_2$ and 90% nitrogen gas was bubbled through the medium to provide both an anaerobic atmosphere and a source of carbonate for succinic acid synthesis, as described in Example 1. The contents of the fermentor were circulated through a EDI apparatus as illustrated in FIG. 1, while applying a potential of about 3 to 12 V per ion-exchange unit across the anode and cathode of the EDI apparatus. The pH of the medium in the fermentor was maintained at about 6 to 7 (e.g., about 6.5 on average) by the controlled addition of NaOH from a recycle tank into the fermentor. The recycle tank contained 0.05 M NaOH at the start the reaction. The positive Na ions in the circulated reaction medium were combined with hydroxyl ions to form NaOH, which transported to a NaOH collection vessel that is at pH of about 11 during operation, which was reused as needed for neutralizing the fermentation broth in the fermentor.

Figure 5:
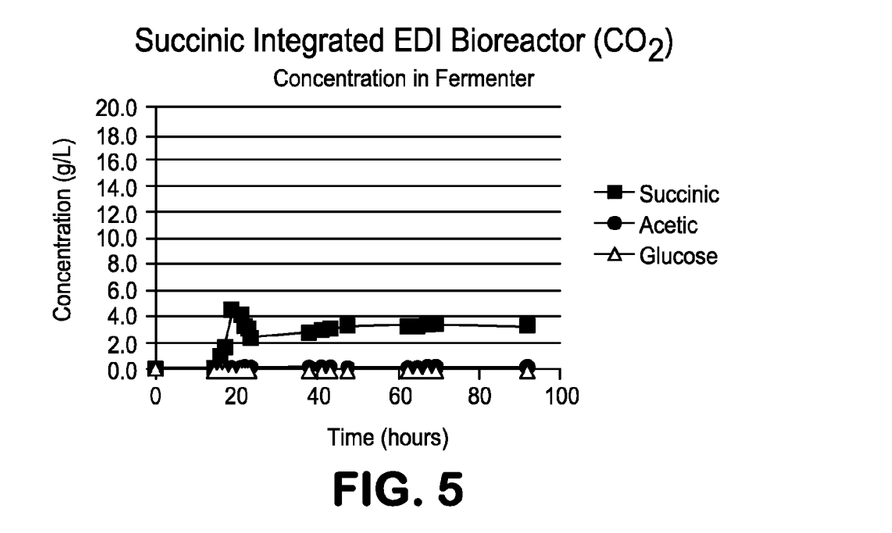
FIG. 5 provides a graph of succinic acid concentration in the fermentation bioreactor 110 of an integrated EDI bioreactor system as illustrated in FIG. 1 using $CO_2$ fed directly into the fermentor as the carbonate source for the fermentation reaction.
Figure 6:
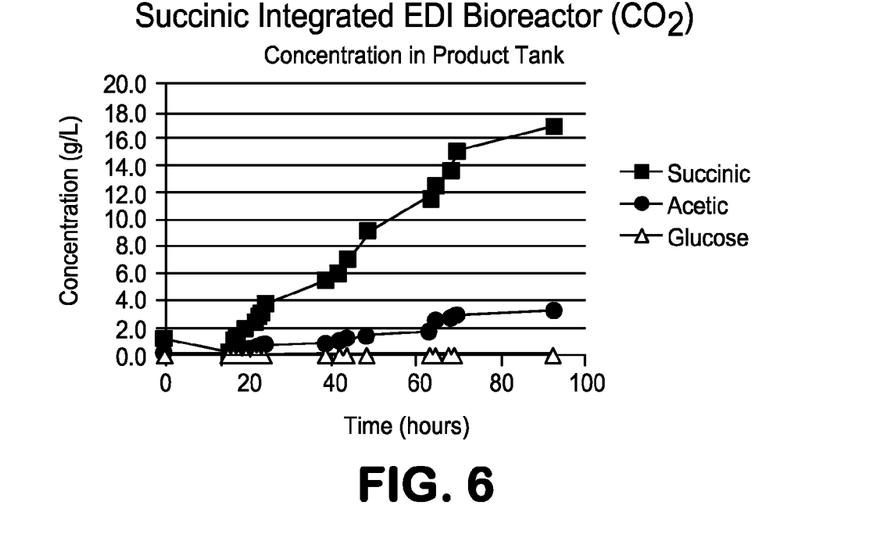
FIG. 6 provides a graph of succinic acid accumulation and concentration in the product collection vessel 122 from an integrated EDI bioreactor system as illustrated in FIG. 1 using $CO_2$ fed directly into the fermentor as the carbonate source for the fermentation reaction.

Samples were prepared for succinic acid assay as described above in Example 1. Samples were taken from both the fermentor and the product collection vessel of the EDI bioreactor system to detect glucose, succinic acid, lactic acid, acetic acid, and ethanol. Samples were also taken to monitor the pH in the fermentor, product tank and NaOH recycle tank. The results of producing succinic acid in an integrated EDI bioreactor system with $CO_2$ addition are shown in FIGS. 5 and 6. The production of succinic acid in the fermentor was monitored for 100 hours. The levels of succinic acid in the bioreactor were maintained at approximately 2-4 grams/liter throughout the run (FIG. 5). The levels of glucose and other fermentation products were very low. The pH in the fermentor was approximately 6.5 during the experiment.

The levels of succinic acid in the EDI device product vessel rose steadily for about 100 hours and reached a level of about 17 grams/liter (FIG. 6). The level of the co-product acetic acid was about 3 grams/liter at 100 hours. This represents a greater than 5-fold selectivity for producing succinic acid over acetic acid in the product stream. The pH in the product vessel was approximately 1.9. The succinic acid product is therefore in the free acid form and not in the form of a Na salt. The pH in the NaOH retention and recycle stream vessel was approximately 11. The retention and recycle of the NaOH from the EDI apparatus provides a continuous resupply of base to control the pH in the bioreactor.

EXAMPLE 3

Continuous Fermentation in EDI Bioreactor with Carbonate Feed

Figure 7:
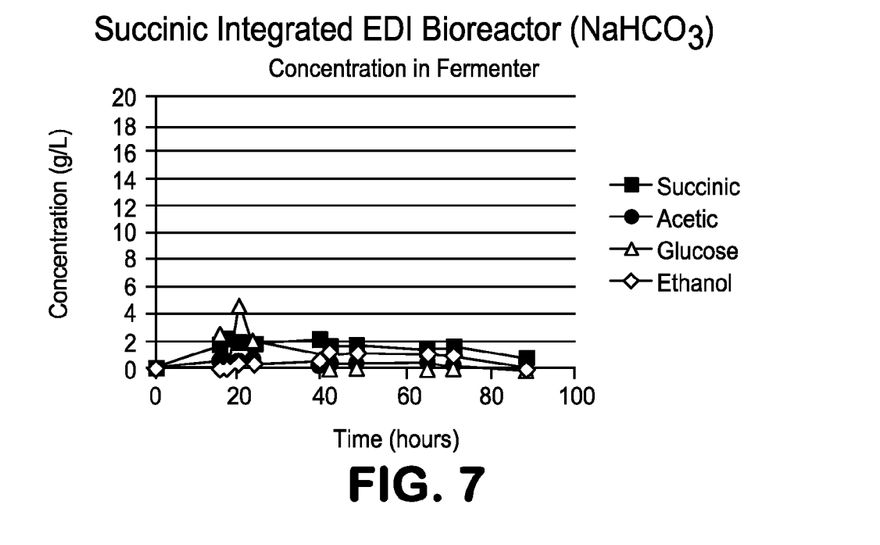
FIG. 7 provides a graph of succinic acid concentration produced in the fermentation bioreactor 210 of an integrated EDI bioreactor system as illustrated in FIG. 2 using $NaHCO_3$ fed into the fermentor as the carbonate source.
Figure 8:
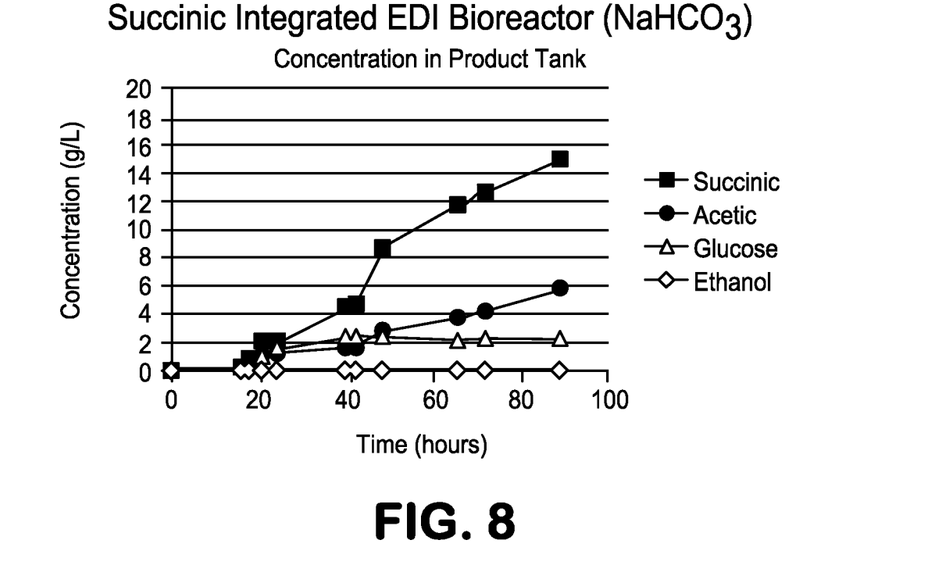
FIG. 8 provides a graph of succinic acid accumulation and concentration in the product collection vessel 222 of an integrated separative bioreactor as illustrated in FIG. 2 using $NaHCO_3$ fed into the fermentor as the carbonate source.

The synthesis of succinic acid in a bioreactor coupled with the capture and concentration of product with an EDI apparatus was examined. The capture and retention of the Na and recycle of the resulting NaOH was described in Example 2. In this embodiment the NaOH in the recycle stream was neutralized with a controlled amount of $CO_2$ to yield carbonate salts (e.g., sodium carbonate and bicarbonate; pH 9) as illustrated in FIG. 2. $CO_2$ was added to the reaction by bubbling $CO_2$ directly into a fermentor vessel with a calibrated pH probe and with a solution of 300 mL 0.05 M NaOH that was also autoclaved to be used in the bioreactor. The bioreactor was prepared with about 250 to 300 mL of 5 mM phosphate and pH adjusted to about pH 6. The pH in the carbonate tank was controlled at about pH 8 to 10 by bubbling $CO_2$ into the tank. The fermentation reaction was initiated by adding inoculum (8 to 10 g wet weight of cells) and feeding a concentrated glucose solution (about 200 g/L to 500 g/L) to the bioreactor. The Na carbonate solution in the base supply tank is reused in the bioreactor with additional glucose substrate to provide a continuous succinic acid production process. This process provides a continuous and controlled supply of carbonate for the fermentation reaction and avoids using the extensive mixing and pressure needed when adding $CO_2$ directly into the fermentation broth. In addition, the retention and recycle of carbonate provides for some internal buffering for the succinic acid that is produced by fermentation. The succinic acid production results are shown in FIGS. 7 and 8. The synthesis of succinic acid in the bioreactor was monitored for about 100 hours. The level of succinic acid in the fermentor was maintained at approximately 1 to 2 grams/liter throughout the run (FIG. 7). The levels of glucose and other fermentation products were very low. The pH in the fermentor was approximately 6.5 during the run.

The levels of succinic acid in the product vessel rose steadily for about 100 hours and reached a level of about 15 grams/liter (FIG. 8). The level of co-produced acetic acid was about 6 grams/liter at 100 hours. This represents a greater than 2 fold selectivity for succinic acid production over acetic acid production in the product stream. The pH in the product vessel was approximately 1.9. The succinic acid product is therefore in the free acid form and not in the form of a Na salt. The pH of the carbonate solution in the base tank was maintained at approximately 9 by controlled $CO_2$ addition. The retention and recycle of the NaOH from the EDI apparatus provided a continuous resupply of base, which was combined with $CO_2$ deliver carbonate to the bioreactor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as The embodiments of the invention in which an exclusive property or privilege is claimed are defined as follows:

1. A method of directly producing the acid form of succinic acid comprising circulating the liquid phase of an aqueous, anaerobic fermentation broth from a fermentor into a stacked ion-exchange assembly of an electrodeionization (EDI) apparatus while applying an electric potential across an anode and cathode of the EDI apparatus and supplying glucose and a carbonate source to the fermentation broth;

wherein:

the EDI apparatus comprises:

(a) an anode;

(b) a cathode;

(c) a stacked ion-exchange assembly between the anode and the cathode, the stacked ion-exchange assembly comprising one or more oriented ion exchange units; and (d) a first bipolar membrane separating the cathode from the stacked ion-exchange assembly;

each ion-exchange unit comprises:

(i) a porous ion-exchange resin wafer including an inlet and an outlet, wherein the inlet and outlet together are adapted to circulate a liquid recycle stream containing the liquid phase of the fermentation broth from the fermentor through the resin wafer and back into the fermentor;

(ii) a first flow-distributing gasket adapted to circulate a product stream through a product reservoir;

(iii) an anion exchange membrane adapted to transport at least a portion of succinate ions present in the fermentation broth from the porous ion-exchange resin wafer into the first flow-distributing gasket; and (iv) a second bipolar ion-exchange membrane adapted to allow protons to migrate toward the cathode and into the product stream to combine with the succinate ions, and to allow hydroxyl ions to migrate toward the anode and into the recycle stream in the resin wafer of an adjacent ion-exchange unit; and in each ion exchange unit, the anion exchange membrane is disposed between the first flow-distributing gasket and the wafer, and the first flow-distributing gasket is disposed between the second bipolar ion-exchange membrane and the anion exchange membrane; each ion exchange unit is oriented with the wafer facing the cathode and the second bipolar ion-exchange membrane facing the anode; and the protons and hydroxyl ions are formed by an electrochemical water splitting reaction on the surface of the first and second bipolar membranes when the electric potential is applied across the anode and the cathode;

the fermentation broth comprises glucose, carbonate ions, and an aqueous suspension of *E. coli* bacteria genetically modified to produce succinic acid from glucose and carbonate, the pH of the fermentation broth being maintained at a pH in the range of about 6 to about 7 by addition of an aqueous base into the fermentor from a base reservoir;

and the liquid phase of the fermentation broth is introduced into the porous ion-exchange resin wafer through the inlet thereof where succinate ions produced by the bacteria in the fermentation broth pass from the porous ion-exchange resin wafer through the anion exchange membrane into the first flow-distributing gasket where the succinate ions are combined with protons from the electrochemical water splitting reaction to form succinic acid that then flows out of the first flow-distributing gasket into the product stream that is circulated into a product collection vessel; and succinate ion-depleted fermentation broth passes through the outlet of the porous ion-exchange wafer into the recycle stream and back into the fermentor;

alkali metal and/or alkaline earth metal ions in the fermentation broth are combined with hydroxyl ions from the water splitting reaction to form a solution of a metal hydroxide, which is recycled into the base reservoir; and the protons and hydroxyl ions generated by the water splitting reaction are separated from each other by the first and second bipolar membranes with the protons migrating toward the cathode and the hydroxyl ions migrating toward the anode.

2. The method of claim 1 wherein the electric potential applied across the anode and cathode is about 3 to 12 Volts per ion-exchange unit.

3. The method of claim 1 wherein the bacteria comprise *Escherichia coli* having mutations in the genes ptsG, pflB, and ldhA which facilitate bioproduction of succinic acid.

4. The method of claim 1 wherein the bacteria comprise an *Escherichia coli* strain selected from the group consisting of AFP 184, AFP 400, AFP 404, and a combination of any of the foregoing strains.

5. The method of claim 1 wherein the bacteria comprise *Escherichia coli* strain AFP 184.

6. The method of claim 1 wherein the source of carbonate is carbon dioxide gas that is introduced directly into the fermentor.

7. The method of claim 1 wherein the source of carbonate is an aqueous carbonate solution comprising carbonate ion, bicarbonate ion, or a combination thereof, that is introduced directly into the fermentor.

8. The method of claim 1 wherein the EDI apparatus further comprises:

(e) a second flow-distributing gasket between the anode and the stacked ion-exchange assembly closest to the anode; and (f) a third flow-distributing gasket between the cathode and the first bipolar membrane.

9. The method of claim 1 wherein the resin wafers of the EDI apparatus comprise cationic and anionic exchange moieties in a ratio of about 1.3:1 anionic-to-cationic.

10. The method of claim 1 wherein the ion-exchange resin in the resin wafers of the EDI apparatus is present at a concentration in the range of about 30 to 80 percent by weight (wt %).

11. The method of claim 1 wherein the ion-exchange resin wafers of the EDI apparatus comprise about 25 wt % to about 45 wt % of a binder.

12. The method of claim 11 wherein the binder is present in a weight ratio to the ion-exchange moieties of about 1:3.

13. The method of claim 1 wherein wafers of the EDI apparatus have a porosity of at least about at least 15%.

14. The method of claim 1 wherein the metal hydroxide comprises sodium hydroxide.

* * * * *